United States Patent
Morgan et al.

(10) Patent No.: US 7,247,464 B2
(45) Date of Patent: Jul. 24, 2007

(54) CSPCI RESTRICTION ENDONUCLEASE

(75) Inventors: Richard Morgan, Middleton, MA (US); Celine Nguefeu Nkenfou, Yaounde (CM)

(73) Assignee: New England Biolabs, Inc., Ipswich, MA (US)

(*) Notice: Subject to any disclaimer, the term of this patent is extended or adjusted under 35 U.S.C. 154(b) by 109 days.

(21) Appl. No.: 11/088,267

(22) Filed: Mar. 23, 2005

(65) Prior Publication Data

US 2005/0233433 A1    Oct. 20, 2005

Related U.S. Application Data

(60) Provisional application No. 60/555,796, filed on Mar. 24, 2004.

(51) Int. Cl.
*C12N 9/22*    (2006.01)

(52) U.S. Cl. ..................................... 435/199

(58) Field of Classification Search ............... None
See application file for complete search history.

(56) References Cited

OTHER PUBLICATIONS

Janulaitis, A., et al. (1983) FEBS Lett. 161(2), 210-212.*
Bitinaite, J.B., et al. (1985) FEBS Lett. 182(2), 509-513.*
Bozic, D., et al. (1996) J. Mol. Biol. 255, 176-186.*
New England BioLabs 2002-2003 catalog, p. 9.*

* cited by examiner

*Primary Examiner*—Charles L. Patterson, Jr.
(74) *Attorney, Agent, or Firm*—Harriet M. Strimpel

(57) ABSTRACT

A novel restriction endonuclease has been identified from *Citrobacter* species 2144 (NEB#1398) which can cleave at nt sequence 5'-CAANNNNGTGG-3' (SEQ ID NO:13) in double-stranded DNA molecules.

2 Claims, 5 Drawing Sheets

Figure 4a
Figure 4b
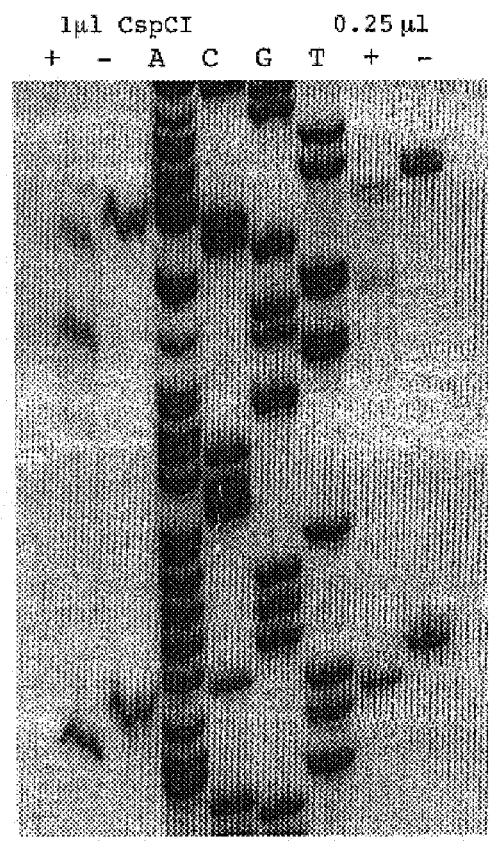
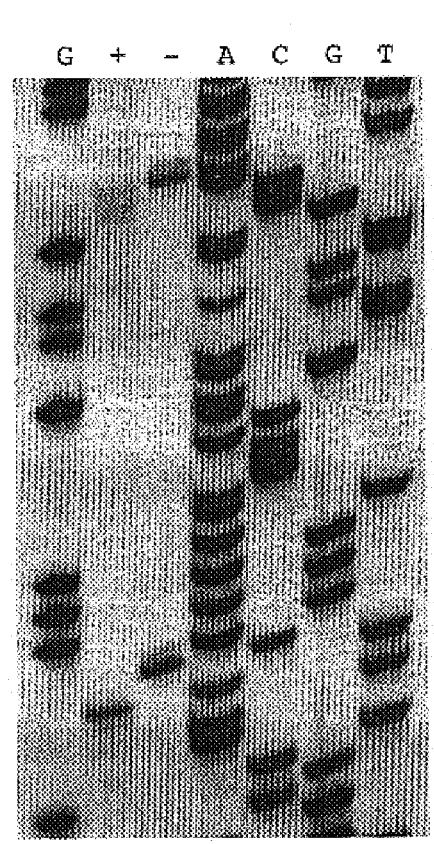

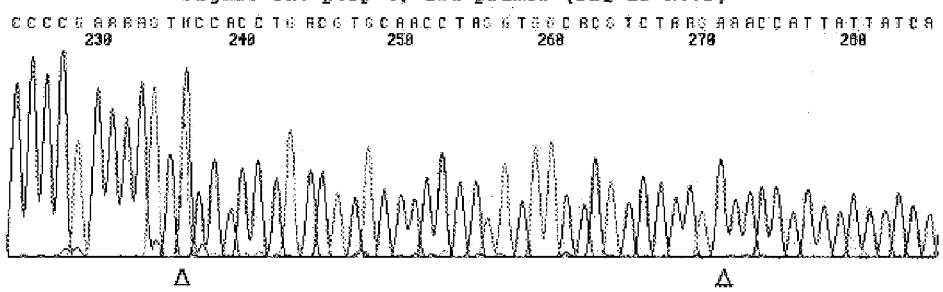
Figure 5a. pCsp-4, fwd primer (SEQ ID NO:5)
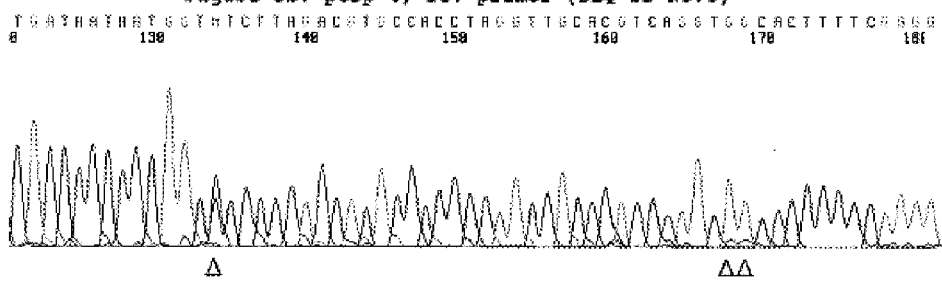
Figure 5b. pCsp-4, rev primer (SEQ ID NO:6)
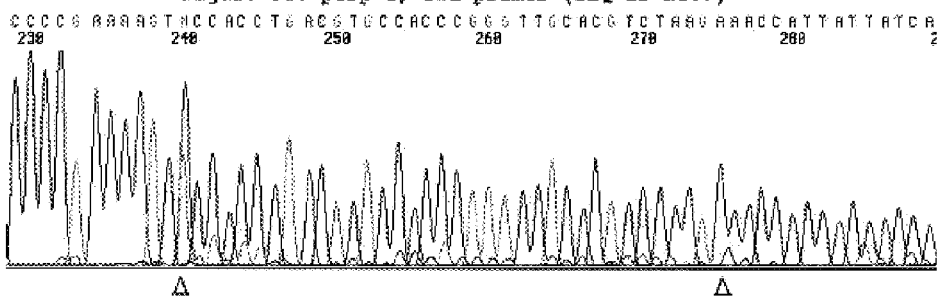
Figure 5c. pCsp-1, fwd primer (SEQ ID NO:7)
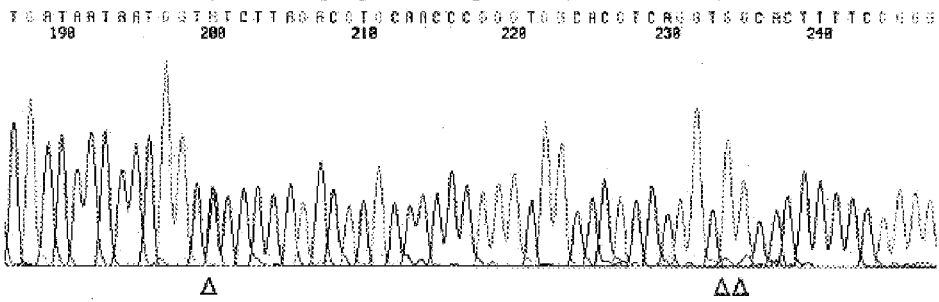
Figure 5d. pCsp-1, rev primer (SEQ ID NO:8)

CSPCI RESTRICTION ENDONUCLEASE

CROSS REFERENCE

This application gains priority from U.S. provisional application No. 60/555,796 filed Mar. 24, 2004, herein incorporated by reference.

BACKGROUND OF THE INVENTION

Restriction endonucleases are enzymes that occur naturally in certain unicellular microbes—mainly bacteria and archaea—and that function to protect those organisms from infections by viruses and other parasitic DNA elements. Restriction endonucleases bind to specific sequences of nucleotides ('recognition sequence') in double-stranded DNA molecules (dsDNA) and cleave the DNA, usually within or close to these sequences, disrupting the DNA and triggering its destruction. Restriction endonucleases usually occur with one or more companion enzymes termed modification methyltransferases. Methyltransferases bind to the same sequences in dsDNA as the restriction endonucleases they accompany, but instead of cleaving the DNA, they alter it by the addition of a methyl group to one of the bases within the sequence. This modification ('methylation') prevents the restriction endonuclease from productively recognizing that site thereafter, rendering the site resistant to cleavage. Methyltransferases function as cellular antagonists to the restriction endonucleases they accompany, protecting the cell's own DNA from destruction by its restriction endonucleases. Together, a restriction endonuclease and its companion modification methyltransferase(s) form a restriction-modification (R-M) system, an enzymatic partnership that accomplishes for microbes what the immune system accomplishes, in some respects, for multicellular organisms.

A large and varied class of restriction endonucleases has been classified as 'Type II' class of restriction endonucleases. These enzymes cleave DNA at defined positions, and when purified can be used to cut DNA molecules into precise fragments for gene cloning and analysis. The biochemical precision of Type II restriction endonucleases far exceeds anything achievable by chemical methods, making these enzymes the reagents sine qua non of molecular biology laboratories. In this capacity as molecular tools for gene dissection Type II restriction endonucleases have had a profound impact on the life sciences and medicine in the past 25 years, transforming the academic and commercial arenas, alike. Their utility has spurred a continuous search for new restriction endonucleases, and a large number have been found: today more than 250 Type II endonucleases are known, each possessing different DNA cleavage characteristics (Roberts, R. J. et al., *Nucl. Acids. Res.* 33:D230--D232 (2005)). (Rebase, http://rebase.neb.com/rebase). The production and purification of these enzymes have also been improved by the cloning and overexpression of the genes that encode them, usually in the context of non-native host cells such as *E. coli*.

Since the various restriction enzymes appear to perform similar biological roles, and share the biochemistry of causing dsDNA breaks, it might be thought that they would resemble one another in amino acid sequence closely. Experience shows this not to be true, however. Surprisingly, far from sharing significant amino acid similarity with one another, most enzymes appear unique, with their amino acid sequences resembling neither other restriction enzymes nor any other known kind of protein. Type II restriction endonucleases seem to have arisen independently of each other during evolution, for the most part, and to have done so hundreds of times, so that today's enzymes represent a heterogeneous collection rather than a discrete family descended from a common ancestor. Restriction endonucleases are biochemically diverse in organization and action: some act as homodimers, some as monomers, others as heterodimers. Some bind symmetric sequences, others asymmetric sequences; some bind continuous sequences, others discontinuous sequences; some bind unique sequences, others multiple sequences. Some are accompanied by a single methyltransferase, others by two, and yet others by none at all. When two methyltransferases are present, sometimes they are separate proteins and at other times they are fused. The orders and orientations of restriction and modification genes vary, with all possible organizations occurring. Several kinds of methyltransferases exist, some methylating adenines, others methylating cytosines at the N-4 position, or at the 5 position). Usually there is no way of predicting, a priori, which modifications will block a particular restriction endonuclease, which kind(s) of methyltransferases(s) will accompany that restriction endonuclease in any specific instance, nor what their gene orders or orientations will be.

From the point of view of cloning a Type II restriction endonuclease, the great variability that exists among R-M systems means that, for experimental purposes, each is unique. Each enzyme is unique in amino acid sequence and catalytic behavior; each occurs in unique enzymatic association, adapted to unique microbial circumstances; and each presents the experimenter with a unique challenge. Sometimes a restriction endonuclease can be cloned and over-expressed in a straightforward manner but very often it cannot, and what works well for one enzyme may fail altogether for the next. Success with one is no guarantee of success with another.

Novel endonucleases provide opportunities for innovative genetic engineering.

SUMMARY OF THE INVENTION

In an embodiment of the invention, substantially pure Type IIG restriction endonuclease obtainable from *Citrobacter* species 2144 (NEB#1398) (ATCC Patent Accession No. PTA-5846) is provided that is further capable of recognizing the following base sequence in double-stranded deoxyribonucleic acid molecules (New England Biolabs, Inc., Beverly, Mass.):

```
5'-  ↓N₁₀CAANNNNNGTGGN₁₂ ↓-3'     (SEQ ID NO:1)

3'-  ↑N₁₂GTTNNNNNCACCN₁₀ ↑-5' and/or

5'-  ↓N₁₀CAANNNNNGTGGN₁₃ ↓-3'     (SEQ ID NO:2)

3'-  ↑N₁₂GTTNNNNNCACCN₁₁ ↑-5' and/or

5'-  ↓N₁₁CAANNNNNGTGGN₁₂ ↓-3'     (SEQ ID NO:3)

3'-  ↑N₁₃GTTNNNNNCACCN₁₀ ↑-5' and/or

5'-  ↓N₁₁CAANNNNNGTGGN₁₃ ↓-3'     (SEQ ID NO:4)

3'-  ↑N₁₃GTTNNNNNCACCN₁₁ ↑-5'
``` and cleaving the DNA on both sides of the recognition sequence at the variable positions as indicated by the arrows.

Figure 1:
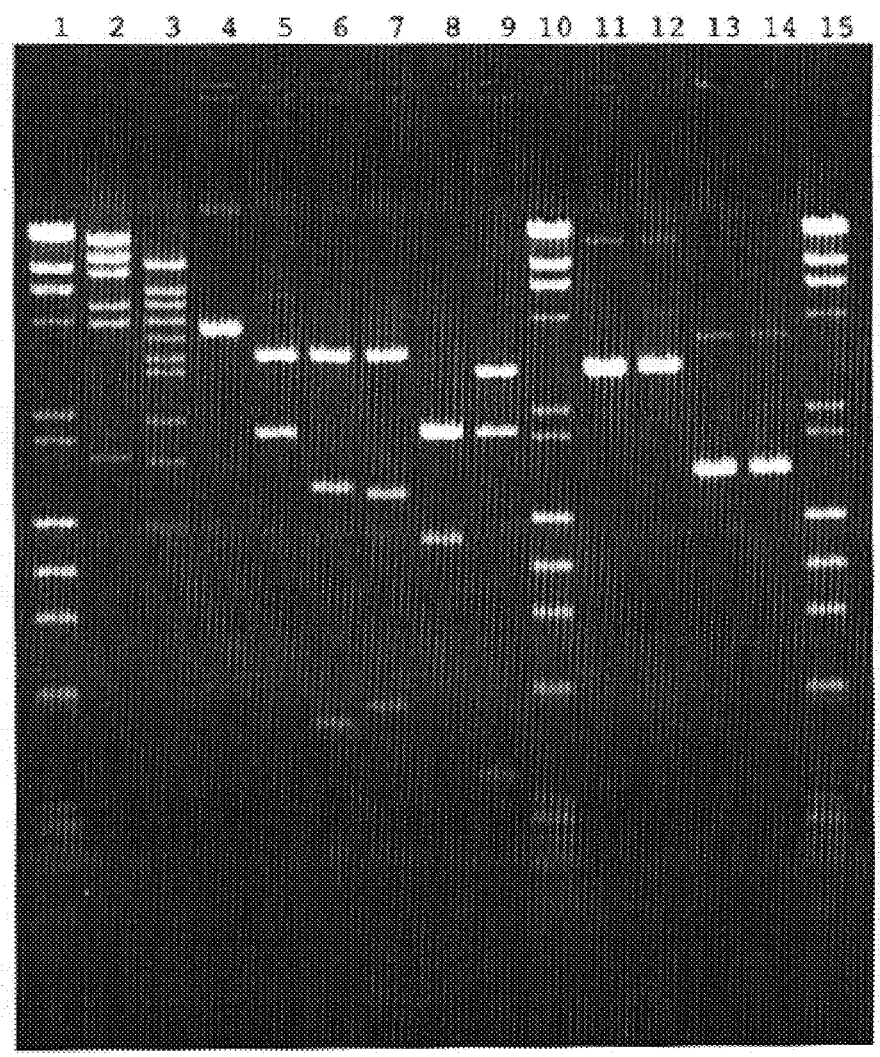
FIG. 1 is an agarose gel showing CspCI-cleavage of phage lambda, T7, PhiX174, pBR322 and pUC19 DNAs. Lanes are as follows.

lanes 1, 10, 15: lambda-HindIII, PhiX174-HaeIII size standards;
lane 2: lambda DNA+CspCI;
lane 3: T7 DNA+CspCI;
lane 4: PhiX174 DNA;
lane 5: PhiX174 DNA+CspCI;
lane 6: PhiX174 DNA+CspCI+PstI;
lane 7: PhiX174 DNA+CspCI+SspI;
lane 8: PhiX174 DNA+CspCI+NciI;
lane 9: PhiX174 DNA+CspCI+StuI;
lane 11: pBR322 DNA;
lane 12: pBR322 DNA+CspCI;
lane 13: pUC19 DNA;
lane 14: pUC19 DNA+CspCI.

Figure 2:
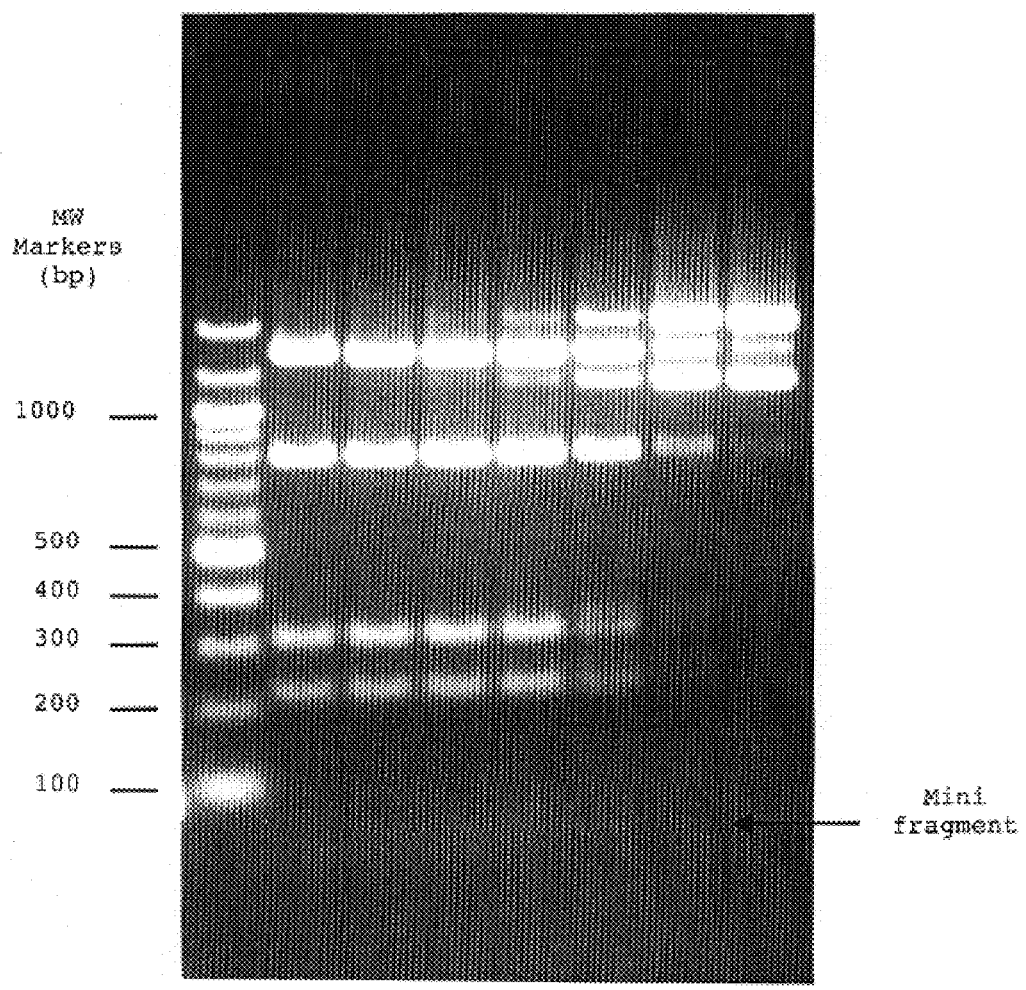

FIG. 2 is a high-concentration agarose gel of CspCI-cleaved pUC2CspC DNA showing 35±1 bp internal 'mini-fragment'.

Figure 3:
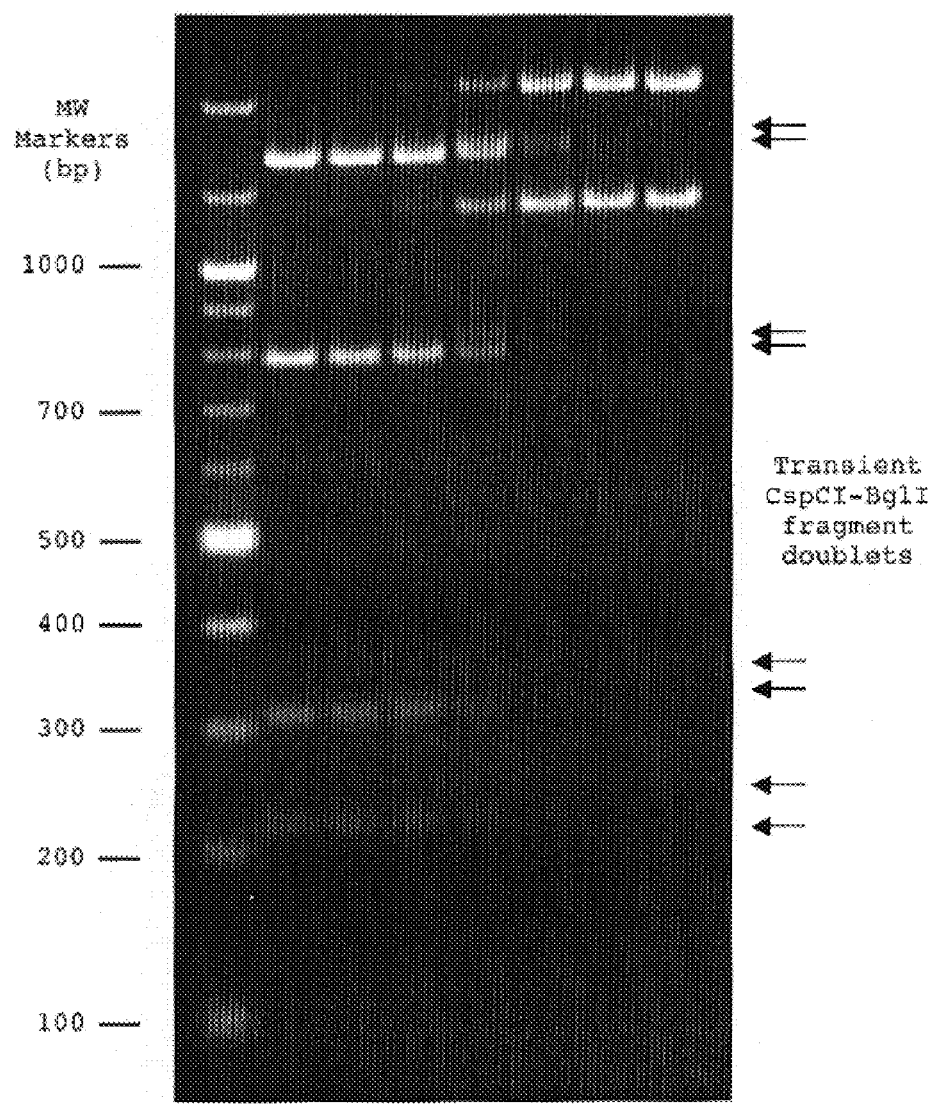

FIG. 3 is a high-resolution agarose gel showing partial-digestion doublet fragments. DNA: BglI-cleaved pUC2CspC re-digested with increasing amounts of CspCI. Transient CspCI-BglI fragment doublets are show by the arrows.

FIGS. 4a and 4b show a determination of the CspCI cleavage sites by primed synthesis. Two experiments were performed using the same M13mp18 template and primer combination.

(−) is CspCI-cleaved DNA only; (+) is Klenow-treatment of the CspCI-cleaved DNA.

FIG. 5 shows a determination of the CspCI cleavage sites by run-off automated sequencing.

FIG. 5a: pUC1CspC-4 template; forward primer (SEQ ID NO:5)

FIG. 5b: pUC1CspC-4 template; reverse primer (SEQ ID NO:6)

FIG. 5c: pUC1CspC-1 template; forward primer (SEQ ID NO:7)

FIG. 5d: pUC1CspC-1 template; reverse primer (SEQ ID NO:8)

A-anomalies, signifying template cleavage, are shown as triangles (Δ) below the tracings.

Isolation of CspCI

CspCI was obtained by culturing either (i) *Citrobacter* species 2144 (NEB#1398) or (ii) the transformed host, *E. coli* NEB#1554, and recovering the endonuclease from the cells. A sample of *Citrobacter* species 2144 (NEB#1398) has been deposited under the terms and conditions of the Budapest Treaty with the American Type Culture Collection (ATCC) on Mar. 4, 2004 and bears the Patent Accession No. PTA-5846 (New England Biolabs, Inc., Beverly, Mass.). A sample of a recombinant strain expressing CspCI, *E. coli* (NEB#1554), has also been deposited under the terms and conditions of the Budapest Treaty with the American Type Culture Collection (ATCC) on Mar. 24, 2004 and bears the Patent Accession No. PTA-5887 (New England Biolabs, Inc., Beverly, Mass.).

*Citrobacter* species 2144 (NEB#1398) or *E. coli* (NEB#1554) was grown in *Escherichia coli* (NEB#1554) using Luria broth media (BBL Microbiology Systems, Cockeysville, Md.) supplemented with 100 mg/ml ampicillin and incubated aerobically at 37° C. Cells in the late logarithmic stage of growth are collected by centrifugation and either disrupted immediately or stored frozen at −70° C. (New England Biolabs, Inc., Beverly, Mass.).

The CspCI endonuclease was isolated from *Citrobacter* species 2144 (NEB#1398) or *Escherichia coli* (NEB#1554, New England Biolabs, Inc., Beverly, Mass.) by conventional protein purification techniques. The cell paste was suspended in a buffer solution and ruptured by sonication, high-pressure dispersion or enzymatic digestion to allow extraction of the endonuclease by the buffer solution. Intact cells and cellular debris are then removed by centrifugation to produce a cell-free extract containing CspCI. The CspCI endonuclease was then purified from the cell-free extract by ion-exchange chromatography, affinity chromatography, molecular sieve chromatography, or a combination of these methods to produce the endonuclease.

Production of Native CspCI Endonuclease 277 grams of *E. coli* NEB#1554 CspCI cell pellet or *Citrobacter* species 2144 (NEB#1398) (New England Biolabs, Inc., Beverly, Mass.) were suspended in 1 liter of Buffer A (20 mM Tris-HCl (pH 7.4), 1.0 mM DTT, 0.1 mM EDTA, 5% Gycerol) containing 300 mM NaCl, and passed through a Gaulin homogenizer at ~12,000 psig. The lysate was centrifuged at ~13,000×G for 40 minutes and the supernatant collected.

The supernatant solution was applied to a 400 ml DEAE Fast-Flow column (GE Healthcare, formerly Amersham Biosciences, Piscataway N.J.) column equilibrated in buffer A plus 300 mM NaCl, and the flow-through, containing the CspCI endonuclease activity, was diluted 1:1 with buffer A.

The diluted enzyme was applied to a 375 ml Heparin Hyper-D column (Biosepra, Marlborough Mass.) which had been equilibrated in buffer B. (20 mM Tris-HCl (pH 7.4), 150 mM NaCl, 1.0 mM DTT, 0.1 mM EDTA, 5% Gycerol). A 2.5 L wash of buffer B was applied, then a 2 L gradient of NaCl from 0.15M to 1M in buffer B was applied and fractions were collected. Fractions were assayed for CspCI endonuclease activity by incubating with 1 microgram of phage lambda DNA (New England Biolabs, Inc., Beverly, Mass.) in 50 microliter NEBuffer 2 (New England Biolabs, Inc., Beverly, Mass.), supplemented with 20 microMolar S-adenosyl-L-methionine (AdoMet) for 15 minutes at 37° C. CspCI activity eluted at 0.3M to 0.35M NaCl.

The Heparin Hyper-D column fractions (Biosepra, Marlborough Mass.) containing the CspCI activity were pooled and load directly onto a 200 ml Ceramic htp column (Biosepra, Marlborough Mass.) equilibrated in Buffer B. A 1 L wash of buffer B was applied, then a 1 L gradient of KHPO$_4$ (pH 7.5) from 0M to 0.6M in buffer B was applied and fractions were collected. Fractions were assayed for CspCI endonuclease activity by incubating with 1 microgram of phage lambda DNA in 50 microliter NEBuffer 2 (New England Biolabs, Inc., Beverly, Mass.), supplemented with 20 microMolar AdoMet for 15 minutes at 37° C. CspCI activity eluted at 0.4M to 0.5M KHPO4.

The Ceramic HTP column fractions containing the CspCI activity were pooled and dialyzed into Buffer C (20 mM Tris-HCl (pH 7.4), 100 mM NaCl, 1.0 mM DTT, 0.1 mM EDTA, 5% Gycerol).

This pool was flowed through a 50 ml Source Q column (GE Healthcare, formerly Amersham Biosciences, Piscataway N.J.) equilibrated in buffer C and directly onto a Heparin TSK equilibrated in buffer C. A 250 ml wash of buffer C was applied, then a 400 ml gradient of NaCl from 0.1M to 0.8 M in buffer C was applied and fractions were collected. Fractions were assayed for CspCI endonuclease activity by incubating with 1 microgram of phage lambda DNA (New England Biolabs, Inc., Beverly, Mass.) in 50 microliter NEBuffer 2 (New England Biolabs, Inc., Beverly, Mass.), supplemented with 20 microMolar AdoMet for 15 minutes at 37° C. CspCI activity eluted at 0.3M to 0.35M NaCl.

The pool was dialyzed into Storage Buffer. (10 mM Tris-HCl (pH 7.4), 100 mM NaCl, 1.0 mM DTT, 0.1 mM EDTA, 50% Gycerol). One million units of CspCI were obtained from this procedure. The CspCI endonuclease thus produced was substantially pure and free of contaminating nucleases. SDS polyacrylamide gel electrophoresis of a sample of this preparation showed it comprised two principal proteins of approximately 70 kDa and 35 kDa in the approximate ratio by mass of 2:1.

Activity Determination

CspCI activity: Samples of from 1 to 10 microliter were added to 50 microliter of substrate solution consisting of 1× NEBuffer 2 (New England Biolabs, Inc., Beverly, Mass.) containing 1 microgram of phage lambda phage DNA supplemented with 20 microMolar AdoMet. The reaction was incubated at 37° C. for 60 minutes. The reaction was terminated by adding 20 microliter of stop solution (50% glycerol, 50 mM EDTA pH 8.0, and 0.02% Bromophenol Blue.) The reaction mixture was applied to a 1% agarose gel and electrophoresed. The bands obtained were identified by comparison with DNA size standards.

Unit Definition: One unit of CspCI is defined as the amount of CspCI required to completely cleave one microgram of phage lambda DNA in a reaction volume of 50 microliter of 1× NEBuffer 2 (New England Biolabs, Inc., Beverly, Mass.) supplemented with 20 microMolar AdoMet, within one hour at 37° C.

Properties of CspCI:

AdoMet: Supplementing the CspCI reaction with 20 mM AdoMet greatly enhanced the activity of the enzyme. In reactions where AdoMet was omitted, the enzyme exhibited less than 5% of the cutting activity it exhibited in the AdoMet-supplemented reactions, indicating that AdoMet is a necessary cofactor for this enzyme.

Activity in various reaction buffers: CspCI was found to be most active in NEBuffer 2+AdoMet, relative to other standard NEBuffers (New England Biolabs, Inc., Beverly, Mass.).

NEBBuffer 2 is 10 mM Tris-HCl, 10 mM $MgCl_2$, 50 mM NaCl, 1 mM dithiothreitol (pH 7.9 at 25° C.)

Digestion at 37° C. for one hour in the following NEBuffers yielded the following approximate percentage cleavage activities relative to NEBuffer 2 (New England Biolabs, Inc., Beverly, Mass.)+20 mM AdoMet:

NEBuffer 1+20 mM AdoMet: 10%
NEBuffer 2+20 mM AdoMet: 100%
NEBuffer 3+20 mM AdoMet: 10%
NEBuffer 4+20 mM AdoMet: 75%
NEBuffer 2−(No AdoMet): <5%

Activity in a 16-hour reaction: 0.5 units of CspCI are required to cut one microgram of phage lambda DNA in a 16-hour digest, compared to one unit that is required to cut one microgram of phage lambda DNA in a one-hour digest.

Temperature: The CspCI unit titer was determined at 37° C. by a one-hour incubation in 1× NEBuffer 2 (New England Biolabs, Inc., Beverly, Mass.) plus 20 microMolar AdoMet. Incubation of CspCI at 70° C. for 20 minutes prior to performing a reaction at 37° C. does not inactivate the enzyme. After heat treatment at 70° C. for 20 minutes, CspCI retains nearly full activity.

Bilateral cleavage: CspCI cleaves DNA on both sides of its recognition sequence. As a result, in addition to producing regular restriction fragments, CspCI cleavage generates small, internal, 'mini-fragments' of 35±1 bp, one from each recognition site. These mini-fragments, which can be visualized by gel electrophoresis (FIG. 2), comprise the recognition sequence and the flanking DNA on each side up to the cut sites. The two cleavage events that produce the mini-fragments appear to proceed separately: cleavage occurs first on one side of the recognition sequence and then later on the other side, rather than on both sides simultaneously. As a result, when partially digested samples of DNA are examined by gel electrophoresis, the DNA fragments appear as doublets or triplets depending on whether the min-fragments have been trimmed yet from their termini (FIG. 3).

Determination of the CspCI Cleavage Site

The location of CspCI-induced cleavage relative to the recognition sequence was determined by two methods, primed synthesis and run-off automated sequencing.

A: Primed Synthesis Method

The locations of CspCI cleavages relative to the recognition sequence was determined by cleavage of a primer extension product, which was then electrophoresed alongside a set of standard dideoxy sequencing reactions produced from the same primer and template. M13mp18 DNA was employed as the template with a primer near the recognition sequence position at 3009. Readable sequence for this primer template combination begins at position 3069 and continues through the CspCI site.

Sequencing Reactions

The sequencing reactions were performed using the Sequenase version 2.0 DNA sequencing kit (GE Healthcare, formerly Amersham Biosciences, Piscataway, N.J.) with modifications for the cleavage site determination. The template and primer were assembled in a 0.5 ml Eppendorf tube by combining 2.5 microliter dH2O, 3 microliter 5× sequencing buffer (200 mM Tris pH 7.5, 250 mM NaCl, 100 mM $MgCl_2$), 8 microliter M13mp18 single-stranded DNA (1.6 microgram) and 1.5 microliter of primer at 3.2 mM concentration. The primer-template solutions were incubated at 65° C. for 2 minutes, then cooled to 37° C. over 20 minutes in a beaker of 65° C. water on the bench top to anneal the primer. The labeling mix (diluted 1:20) and T7 Sequenase polymerase (GE Healthcare, formerly Amersham Biosciences, Piscataway, N.J.) were diluted according to manufacturer's instructions. The annealed primer and template tube was placed on ice. To this tube were added 1.5 microliter 100 mM DTT, 3 microliter diluted dGTP labeling mix, 1 microliter [a-$^{33}$P] dATP (2000 Ci/mmole, 10 mCi/ml) and 3 microliter diluted T7 Sequenase polymerase (GE Healthcare, formerly Amersham Biosciences, Piscataway, N.J.). The reaction was mixed and incubated at room temperature for 4 minutes.

3.5 microliter of this reaction was then transferred into each of four tubes containing 2.5 microliter termination mix for the A, C, G and T sequencing termination reactions. To the remaining reaction was added to 10 microliter of Sequence Extending Mix, which is a mixture of dNTPs (no ddNTPs) to allow extension of the primer through and well beyond the CspCI site with no terminations to create a labeled strand of DNA extending through the CspCI recognition site for subsequent cleavage. The reactions were incubated 5 minutes at 37° C. To the A, C, G and T reactions were added 4 microliter of stop solution and the samples were stored on ice. The extension reaction was then incubated at 70° C. for 20 minutes to inactivate the DNA polymerase (Sequenase, GE Healthcare, formerly Amersham Biosciences, Piscataway, N.J.), then cooled on ice.

10 microliter of the extension reaction was then placed in one 0.5 ml Eppendorf tube and 7 microliter was placed in a second tube. To the first tube was added 1 microliter (approximately 0.5 unit) of CspCI endonuclease, The reaction was mixed, and then 2 microliter was transferred to the second tube. These enzyme digest reactions were mixed and then incubated at 37° C. for 1 hour, following which the reactions were divided in half. To one half, 4 microliter of stop solution was added and mixed (the 'minus' polymerase reaction). To the second half, 0.4 microliter Klenow DNA polymerase (NEB#210, New England Biolabs, Inc., Beverly, Mass.) containing 80 mM dNTPs was added (the 'plus' reaction), and the reaction was incubated at room temperature for 15 minutes, following which 4 microliter of stop solution was added.

The sequencing reaction products were electrophoresed on an 6% Bis-Acrylamide sequencing gel (Stratagene Corporation, La Jolla, Calif.), with the CspCI digestions of the extension reaction next to the set of sequencing reactions produced from the same primer and template combination.

Results

Digestion of the extension reaction product (the 'minus' reaction) produced a band which co-migrated with the C residue 12 bases 5' to the CspCI recognition sequence, 5'-CAGAGAGATAACCCACAAGAATTG-3', (SEQ ID NO:9) indicating cleavage between the $12^{th}$ and $11^{th}$ bases 5' of the recognition sequence on this strand. A second band was produced which co-migrated with the A residue 12 bases 3' to the CspCI recognition site on this strand, CCACAAGAATTGAGTTAAGCCCAA (SEQ ID NO:10), indicating cleavage between the $12^{th}$ and $13^{th}$ bases 3' to the recognition site. There was also a faint band one base farther from the recognition site, indicating that a small portion of the molecules were cut between the $13^{th}$ and $14^{th}$ bases 3' to the recognition sequence. Treatment of the cleaved extension reaction product with Klenow DNA polymerase (the 'plus' reaction) produced a band two bases shorter than the first band described above, which co-migrated with the A residue 14 bases 5' to the recognition sequence; 5'-ATCGAGAGATAACCCACAAGAATTG-3' (SEQ ID NO:11), indicating cleavage between the $13^{th}$ and $14^{th}$ bases 3' to the recognition sequence on the opposite strand of the DNA (5'-CAANNNNNGTGG($N_{13}$) (SEQ ID NO:12). Several additional bands were observed in the 'plus' lane as well, corresponding to the original band, 12 bases 3' to the site, and bands one and two bases shorter, produced from cuts on the opposite strand of DNA closer to the recognition sequence (FIG. 4).

These results, when combined with those obtained by the second method described below, indicate that CspCI cleaves DNA on both sides of its recognition sequence, and can do so at either N11/N13 or N10/N12 5' to the sequence 5'-CAANNNNNGTGG-3' (SEQ ID NO:13) and at N13/N11 or N12/N10 3' to the sequence, to produce DNA fragments with 2-base 3'-extensions, and an excised fragment of 34, 35 or 36 bases that contains the recognition site.

B: Run-Off Sequencing Method

The second approach employed automated sequencing of CspCI-partially cleaved template DNA with forward and reverse primers to produce sequencing traces that extended through the sites of cleavage. Two plasmids served as templates, pUC1CspC-1 and pUC1CspC-4, constructed by inserting an oligonucleotide containing the CspCI recogni tion sequence into the AatII site at nt 2617 of pUC19 in both orientations.

CspCI-cleavage of pUC1CspC-1 and pUC1CspC-4

Sequencing reactions were carried out on partial digests of pUC1CspC-1 and pUC1CspC-4, in order to determine the sites of cleavage on both sides of the recognition site.

The digests were performed as follows:
a. Combine:
  25 microgram pUC1CspC-1 or pUC1CspC-4
  100 microliter NEBuffer2 (New England Biolabs, Inc., Beverly, Mass.)
  1 microliter 32 mM AdoMet
  dH2O to 1000 microliter
b. Distribute the mixture: 200 microliter in one reaction tube, 100 microliter in 8 subsequent tubes.
c. Add 160 units CspCI endonuclease to the first tube, mix, remove 100 microliter and add it to the second tube, mix, remove 100 microliter and add it to the third tube, etc. until the 9th tube is reached.
d. Incubate all 9 reactions at 37° C. for 60 minutes, then place on ice.
e. Analyze a sample of each reaction on agarose gel; select completely cleaved and partially cleaved plasmids.
f. Purify the cleaved plasmids for sequencing using Zymo DNA Clean and Concentrator-5 spin-columns according to the manufacturer's recommendations (Zymo Research, Orange, Calif.).

Sequencing Reactions

The reactions were performed with an ABI377 DNA sequencer using CspCI-cleaved pUC1CspC-1 and -4 plasmid templates, and a pair of primers that initiate synthesis approximately 250 nt away from the CspCI site on one side, (forward-primer), and 160 nt away from the CspCI site on the other side (reverse primer). The sequences of these two primers are:

5'-CAGTTCGATGTAACCCACTCG-3'    (SEQ ID NO:14)

forward primer; corresponds to pUC19 nt 2346–2366; interrogates the minus-strand of the vector

5'-CCCGCTGACGCGCCCTGACGGGC-3'    (SEQ ID NO:15)

reverse primer; corresponds to pUC19 nt 96–118 complement; interrogates the plus-strand of the vector When sequencing reactions encounter the 5' end of a template strand, they frequently add a final, non-templated A to the synthesized strand. If the template DNA comprises a mixture of intact and truncated strands, such as occurs in incompletely cleaved DNA samples, the position of cleavage reveals itself in the sequencing trace by an anomalous A peak superimposed on the normal peak, and by an overall reduction in the heights of the following peaks. If the base normally present at the position of the anomaly is something other than A–G, for example—then a mixed signal is seen, in this example G plus A. However, if the base normally present at this position is also A, then a single A peak is seen, perhaps higher than normal, and this confounds unambiguous identification.

Results

Unambiguous results were obtained for the positions of cleavage on the 5' sides of the recognition sequence, but the data was poorer regarding cleavage on the 3' sides. As a whole, however, they were consistent with the endonuclease cleaving to produce fragments with 2-base 3'-overhangs at. Sequence traces from representative reactions are shown in FIG. 5.

The reaction of partially cleaved pUC1CspC-4 with the forward primer displayed a strong anomalous A superimposed on the G 13 nt before the recognition sequence, and a stronger-than-expected A peak 11 nt after it:

5' . . . AAGTGccacctgacgt<u>gcaa</u>cctag<u>gtgg</u>cacgtctaagaaac . . . (SEQ ID NO:16)

(Notation. Underlined: CspCI recognition site; bold: normal base over which anomalous A superimposed; UPPER CASE: peaks of normal height; lower case: peaks of reduced height)

These results suggest that cleavage of the complementary strand (indicated |) occurs:

5' . . . GTTT|CTTAGACGTG<u>CCAC</u>CTAG<u>GTTG</u>CACGTCAGGTGGC|ACTT . . . (SEQ ID NO:17)

The reaction of partially cleaved pUC1CspC-4 with the reverse primer displayed a strong A-anomaly on the T 12 nt before the recognition sequence, and a suggestion of two anomalous A's under the two G's 11 and 12 nt after the sequence:

5' . . . TGGTTtcttagacgtg<u>ccac</u>ctag<u>gttg</u>cacgtcaggtggcact . . . (SEQ ID NO:18)

Ignoring momentarily the G-11 anomaly, these results suggests that cleavage of the complementary strand occurs:

5' . . . TGC|CACCTGACGTG<u>CAA</u>CCTAG<u>GTGG</u>CACGTCTAAGAA|ACCA . . . (SEQ ID NO:19)

Combining these results, CspCI-cleavage at the site in pUC1CspC-4 appears to be:

5' . . . AGTGC|CACCTGACGTG<u>CAA</u>CCTAG<u>GTGG</u>CACGTCTAAGAA|ACC . . . (SEQ ID NO:20)
3' . . . TCA|CGGTGGACTGCAC<u>GTT</u>GGATC<u>CAC</u>CGTGCAGATTC|TTTGG . . .

That is to say: 11/13 CAA $N_5$ GTGG 12/10 (SEQ ID NO:13)

The same G-13 and A-11 A-anomalies were seen when partially-cleaved pUC1CspC-1 was interrogated the forward primer, and the same T-12 A-anomaly was seen when it was interrogated with the reverse primer. Consequently, cleavage at the site in pUC1CspC-1 appears to be:

5' . . . AGTGC|CACCTGACGTGCCACCCGGGTTGCACGTCTAAGAA|ACC . . . (SEQ ID NO:21)
3' . . . TCA|CGGTGGACTGCACGGTGGGCCCAACGTGCAGATTC|TTTGG . . .

That is to say: 10/12 CAA $N_5$ GTGG 13/11 (SEQ ID NO:13)

This numerical reversal in cleavage distances indicates that the positions of DNA cleavage are independent of recognition-sequence orientation, and dependent on nature of flanking sequence. The sequence to the left (counter-clockwise) of the recognition site is the same in both plasmids, as also is the sequence to the right (clockwise). The latter, which is somewhat A:T-rich, would seem to be more extended, physically, than the G:C-rich DNA to the left, such that the endonuclease, as it 'measures' out from its binding site, cleaves 12/10 on either side if the DNA is extended, and 13/11 on either side if the DNA is compact.

Returning to the G-11 anomaly momentarily ignored, above, its presence in the pUC1CspC-4/reverse primer reaction suggests that the otherwise compact leftward DNA can become more extended, perhaps due to torsional relaxation that accompanies supercoil-release during digestion, leading to 10/12 cleavage at this location, also. This confirms to a degree that CspCI can also cleave:

10/12 CAA $N_5$ GTGG 12/10 (SEQ ID NO:13), and by extension, 11/13 CAA $N_5$ GTGG 13/11 (SEQ ID NO:13).

What is claimed is:

1. A substantially pure CspCI restriction endonuclease obtainable from *Citrobacter* species 2144 (ATCC Patent Accession No. PTA-5846).

2. A substantially pure restriction endonuclease according to claim 1 capable of recognizing at least one sequence selected from the group consisting of SEQ ID NO:1, SEQ ID NO:2, SEQ ID NO:3 and SEQ ID NO:4, and cleaving the DNA on both sides of the recognition sequence.

* * * * *

SEQUENCE LISTING

<160> NUMBER OF SEQ ID NOS: 21

<210> SEQ ID NO 1
<211> LENGTH: 34
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (1)..(10)
<223> OTHER INFORMATION: n=a,c,g or t
<220> FEATURE:
<221> NAME/KEY: misc_feature
<222> LOCATION: (14)..(18)
<223> OTHER INFORMATION: n=a,c,g or t
<220> FEATURE:
<221> NAME/KEY: misc_feature
<222> LOCATION: (23)..(34)
<223> OTHER INFORMATION: n=a,c,g or t

<400> SEQUENCE: 1
nnnnnnnnnn caannnnngt ggnnnnnnnn nnnn                              34

<210> SEQ ID NO 2
<211> LENGTH: 35
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (1)..(10)
<223> OTHER INFORMATION: n=a,c,t or g
<220> FEATURE:
<221> NAME/KEY: misc_feature
<222> LOCATION: (14)..(18)
<223> OTHER INFORMATION: n=a,c,t or g
<220> FEATURE:
<221> NAME/KEY: misc_feature
<222> LOCATION: (23)..(35)
<223> OTHER INFORMATION: n=a,c,t or g

<400> SEQUENCE: 2
nnnnnnnnnn caannnnngt ggnnnnnnnn nnnnn                             35

<210> SEQ ID NO 3
<211> LENGTH: 35
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (15)..(19)
<223> OTHER INFORMATION: n is a, c, g, or t
<220> FEATURE:
<221> NAME/KEY: misc_feature
<222> LOCATION: (24)..(35)
<223> OTHER INFORMATION: n is a, c, g, or t

<400> SEQUENCE: 3
nnnnnnnnnn ncaannnnng tggnnnnnnn nnnnn                             35

<210> SEQ ID NO 4
<211> LENGTH: 36

```
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (1)..(11)
<223> OTHER INFORMATION: n=a,c,t or g
<220> FEATURE:
<221> NAME/KEY: misc_feature
<222> LOCATION: (15)..(19)
<223> OTHER INFORMATION: n=a,c,t or g
<220> FEATURE:
<221> NAME/KEY: misc_feature
<222> LOCATION: (24)..(36)
<223> OTHER INFORMATION: n=a,c,t or g

<400> SEQUENCE: 4
nnnnnnnnnn ncaannnnng tggnnnnnnn nnnnnn                    36

<210> SEQ ID NO 5
<211> LENGTH: 61
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (12)..(12)
<223> OTHER INFORMATION: n=a,c, g or t

<400> SEQUENCE: 5
ccccgaaaag tnccacctga cgtgcaacct aggtggcacg tctaagaaac cattattatc    60
a                                                                   61

<210> SEQ ID NO 6
<211> LENGTH: 61
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (14)..(14)
<223> OTHER INFORMATION: n=a,c, g or t

<400> SEQUENCE: 6
tgataataat ggtntcttag acgtgccacc taggttgcac gtcaggtggc acttttcggg    60
g                                                                   61

<210> SEQ ID NO 7
<211> LENGTH: 61
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (12)..(12)
<223> OTHER INFORMATION: n=a,c,t or g

<400> SEQUENCE: 7
ccccgaaaag tnccacctga cgtgccaccc gggttgcacg tctaagaaac cattattatc    60
a                                                                   61

<210> SEQ ID NO 8
<211> LENGTH: 61
<212> TYPE: DNA
```

```
<213> ORGANISM: unknown
<220> FEATURE:
<223> OTHER INFORMATION: synthetic
<220> FEATURE:
<221> NAME/KEY: misc_feature
<222> LOCATION: (14)..(14)
<223> OTHER INFORMATION: n-a,c,g or t

<400> SEQUENCE: 8
tgataataat ggtntcttag acgtgcaacc cgggtggcac gtcaggtggc acttttcggg      60
g                                                                     61

<210> SEQ ID NO 9
<211> LENGTH: 23
<212> TYPE: DNA
<213> ORGANISM: unknown
<220> FEATURE:
<223> OTHER INFORMATION: synthetic

<400> SEQUENCE: 9
cagagagata acccacaaga ttg                                             23

<210> SEQ ID NO 10
<211> LENGTH: 24
<212> TYPE: DNA
<213> ORGANISM: unknown
<220> FEATURE:
<223> OTHER INFORMATION: synthetic

<400> SEQUENCE: 10
ccacaagaat tgagttaagc ccaa                                            24

<210> SEQ ID NO 11
<211> LENGTH: 25
<212> TYPE: DNA
<213> ORGANISM: unknown
<220> FEATURE:
<223> OTHER INFORMATION: synthetic

<400> SEQUENCE: 11
atcgagagat aacccacaag aattg                                           25

<210> SEQ ID NO 12
<211> LENGTH: 25
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (4)..(8)
<223> OTHER INFORMATION: n=a,c,t or g
<220> FEATURE:
<221> NAME/KEY: misc_feature
<222> LOCATION: (13)..(25)
<223> OTHER INFORMATION: n=a,c,t or g

<400> SEQUENCE: 12 caannnngt ggnnnnnnnn nnnnn                                            25

<210> SEQ ID NO 13
<211> LENGTH: 12
<212> TYPE: DNA
<213> ORGANISM: unknown
<220> FEATURE:
<223> OTHER INFORMATION: synthetic
<220> FEATURE:
<221> NAME/KEY: misc_feature
```

```
<222> LOCATION: (4)..(8)
<223> OTHER INFORMATION: n=a,t,c or g

<400> SEQUENCE: 13
caannnnngt gg                                                       12

<210> SEQ ID NO 14
<211> LENGTH: 21
<212> TYPE: DNA
<213> ORGANISM: unknown
<220> FEATURE:
<223> OTHER INFORMATION: primer

<400> SEQUENCE: 14
cagttcgatg taacccactc g                                             21

<210> SEQ ID NO 15
<211> LENGTH: 23
<212> TYPE: DNA
<213> ORGANISM: unknown
<220> FEATURE:
<223> OTHER INFORMATION: primer

<400> SEQUENCE: 15
cccgctgacg cgccctgacg ggc                                           23

<210> SEQ ID NO 16
<211> LENGTH: 43
<212> TYPE: DNA
<213> ORGANISM: unknown
<220> FEATURE:
<223> OTHER INFORMATION: synthetic

<400> SEQUENCE: 16
aagtgccacc tgacgtgcaa cctaggtggc acgtctaaga aac                     43

<210> SEQ ID NO 17
<211> LENGTH: 43
<212> TYPE: DNA
<213> ORGANISM: unknown
<220> FEATURE:
<223> OTHER INFORMATION: synthetic

<400> SEQUENCE: 17
gtttcttaga cgtgccacct aggttgcacg tcaggtggca ctt                     43

<210> SEQ ID NO 18
<211> LENGTH: 44
<212> TYPE: DNA
<213> ORGANISM: unknown
<220> FEATURE:
<223> OTHER INFORMATION: synthetic

<400> SEQUENCE: 18
tggtttctta gacgtgccac ctaggttgca cgtcaggtgg cact                    44

<210> SEQ ID NO 19
<211> LENGTH: 42
<212> TYPE: DNA
<213> ORGANISM: unknown
<220> FEATURE:
<223> OTHER INFORMATION: synthetic

<400> SEQUENCE: 19
tgccacctga cgtgcaacct aggtggcacg tctaagaaac ca                      42
```

```
<210> SEQ ID NO 20
<211> LENGTH: 43
<212> TYPE: DNA
<213> ORGANISM: unknown
<220> FEATURE:
<223> OTHER INFORMATION: synthetic

<400> SEQUENCE: 20
agtgccacct gacgtgcaac ctaggtggca cgtctaagaa acc        43

<210> SEQ ID NO 21
<211> LENGTH: 43
<212> TYPE: DNA
<213> ORGANISM: unknown
<220> FEATURE:
<223> OTHER INFORMATION: synthetic

<400> SEQUENCE: 21
agtgccacct gacgtgccac ccgggttgca cgtctaagaa acc        43
```